US00PP29258P3

(12) United States Plant Patent
Smith

(10) Patent No.: US PP29,258 P3
(45) Date of Patent: Apr. 24, 2018

(54) ***CHRYSANTHEMUM* PLANT NAMED 'CIFZ00034'**

(50) Latin Name: *Chrysanthemum×morifolium*
Varietal Denomination: CIFZ00034

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 35 days.

(21) Appl. No.: 14/999,737

(22) Filed: Jun. 21, 2016

(65) Prior Publication Data

US 2017/0367236 P1 Dec. 21, 2017

(51) Int. Cl.
*A01H 5/02* (2018.01)

(52) U.S. Cl.
USPC ..... Plt./289
CPC ..... *A01H 5/0255* (2013.01)

(58) Field of Classification Search
USPC ..... Plt./289
See application file for complete search history.

(56) References Cited

PUBLICATIONS

UPOV hit on *Chrysanthemum* plant named 'CIFZ00034', QZ PBR 2015/1411, filed Jun. 23, 2015.*

* cited by examiner

*Primary Examiner* — Anne Marie Grunberg
(74) *Attorney, Agent, or Firm* — Dale Skalla

(57) ABSTRACT

A new garden type *Chrysanthemum* plant named 'CIFZ00034' particularly distinguished by the medium to large yellow decorative flowers, compact to medium sized plant with round mound habit, and a natural flowering response in mid-October.

1 Drawing Sheet

Latin name of the genus and species of the plant claimed: *Chrysanthemum×morifolium.*

Varietal denomination: 'CIFZ00034'.

BACKGROUND OF THE NEW PLANT

The present invention comprises a new *Chrysanthemum*, botanically known as *Chrysanthemum×morifolium*, and hereinafter referred to by the variety name 'CIFZ00034'.

'CIFZ00034' is a product of a planned breeding program. The new cultivar has medium to large yellow decorative flowers, compact to medium sized plant with round mound habit, and a natural flowering response in mid-October.

'CIFZ00034' originated from a mutation: stock x-rayed at 1750 RAD in October of 2012, single cutting sport from the stock. The female parent, or mutation parent, was the unpatented, '09-M188', with similar flower type and size but bronzy-yellow not clear yellow like 'CIFZ00034'. Similar plant habit but smaller plant size. Similar blackcloth and natural season response when compared to 'CIFZ00034'. No male parent.

The resultant propagation was in May 2013 in Gilroy, Calif.

The first act of asexual reproduction of 'CIFZ00034' was accomplished when vegetative cuttings were propagated from the initial selection, this asexual reproduction took place on Apr. 9, 2013 in a greenhouse in Gilroy, Calif.

BRIEF SUMMARY OF INVENTION

Horticultural examination of plants grown from cuttings of the plant initiated in May 2013, and continuing thereafter, has demonstrated that the combination of characteristics as herein disclosed for 'CIFZ00034' are firmly fixed and are retained through successive generations of asexual reproduction.

'CIFZ00034' has not been observed under all possible environmental conditions. The phenotype may vary significantly with variations in environment such as temperature, light intensity and day length.

A Plant Breeder's Right for this cultivar was applied for in the European Union on Jun. 23, 2015, No. 2015/1411. 'CIFZ00034' has not been made publicly available prior to the effective filing date of this application, notwithstanding any disclosure that may have been made less than one year prior to the effective filing date of this application by the inventor or another who obtained 'CIFZ00034' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ00034' with colors being as true as possible with an illustration of this type. The photographic drawing shows in FIG. 1 a close view of flower of the new variety and in FIG. 2 a flowering plant from a backcloth trial.

Figure 1:
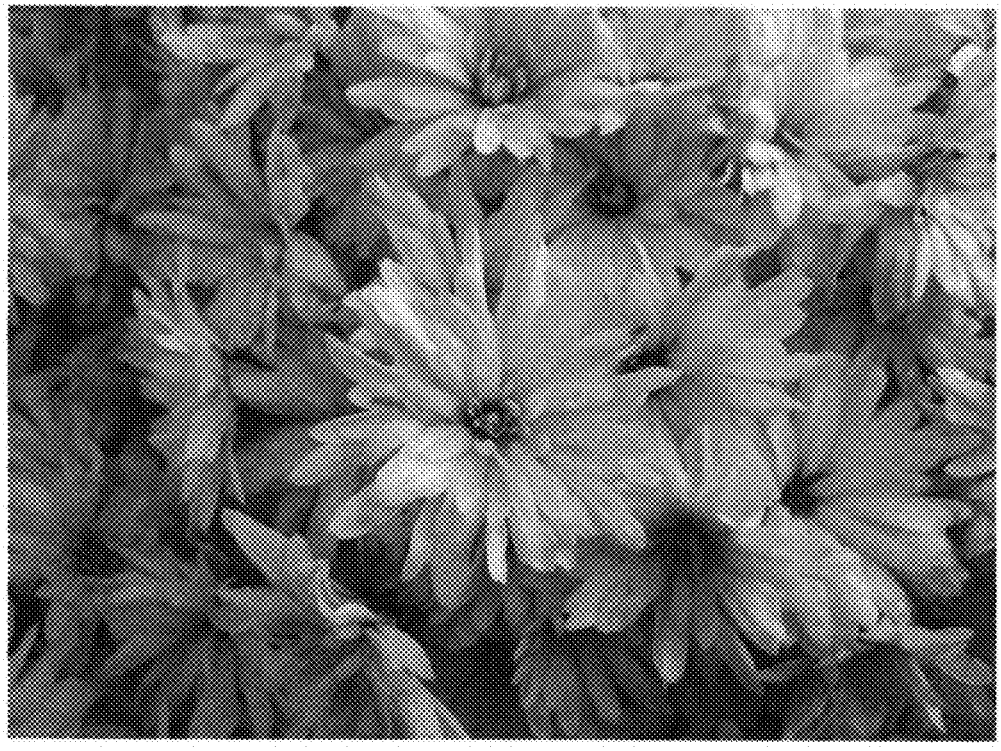
Figure 2:
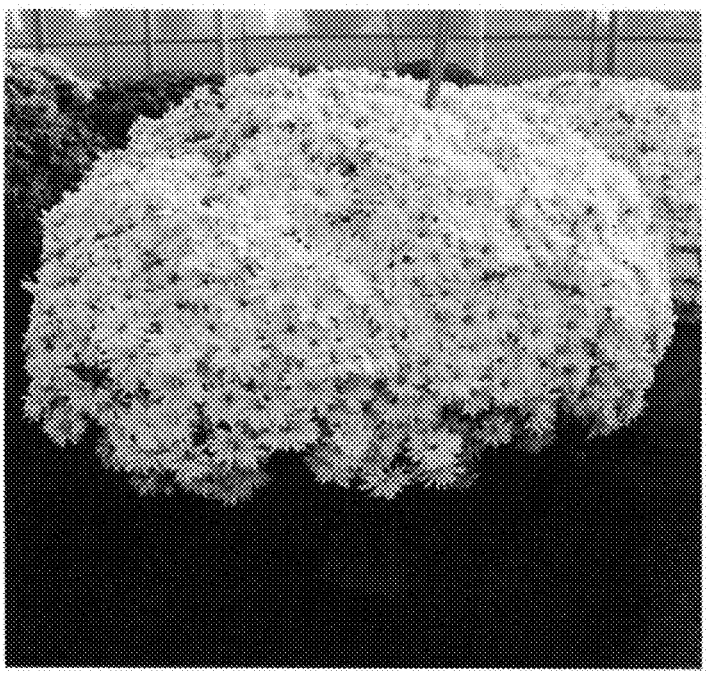

The aforementioned photographs: FIG. 1 was taken in mid-September 2015 and FIG. 2 was taken on the same day, both showing a plant from the same blackcloth outdoor trial in Enkhuizen, The Netherlands.

These plants were about 16 weeks of age. One rooted cutting in a 19 cm pot had been planted in week 23, no pinch. Plants started flowering by about end August.

DETAILED BOTANICAL DESCRIPTION

The measurements were taken in Enkhuizen, The Netherlands, in September 2015 on plants that were growing in 19 cm pot size. Blackcloth trial: shade from week 29 until week 34. Unrooted cuttings were stuck in propagation week 21 and transplanted to the final pots week 23 in Enkhuizen, The Netherlands. Plants were grown without pinching.

Color references are made to The Royal Horticultural Society Colour Chart (R.H.S.) 2001.

TABLE 1

DIFFERENCES BETWEEN THE NEW VARIETY 'CIFZ00034' AND A MOST SIMILAR VARIETY

| | 'CIFZ00034' | 'Golden Yoandrea' (U.S. Plant Pat. No. 16,384) |
|---|---|---|
| Flowering response (blackcloth): | 1 week slower | 1 week faster |
| Flowering response (natural): | ½ week slower | ½ week faster |
| Flower color: | One-tone color | 2-tone color |
| Flower shape: | Similar flower type | Similar flower type |
| Flower size: | Larger | Smaller |
| Plants, stems, flexibility: | Less spread and stronger | More spread and brittle |
| Plant habit or size: | Fuller habit, Smaller plant | Less fuller, Bigger plant |

Plant:
- *Form, growth and habit.*—Herbaceous garden-type, stems upright and outwardly spreading, freely branching, strong and moderately vigorous growth habit.
- *Plant height (above soil).*—20 cm.
- *Plant height (inflorescence included).*—30-32 cm.
- *Plant width.*—50-52 cm.

Roots:
- *Number of days to initiate roots.*—About 4 days at about 22 degrees C.
- *Number of days to produce a rooted cutting.*—14-16 days at 22 degrees C.
- *Type.*—Fine, fibrous, free branching.
- *Color.*—RHS N155B but whiter.

Foliage:
- *Arrangement.*—Alternate.
- *Immature leaf, color upper surface.*—RHS 137A.
- *Immature leaf, color lower surface.*—RHS 137B.
- *Mature leaf, color, upper surface.*—RHS 137A.
- *Mature leaf, color lower surface.*—RHS 137B.
- *Length.*—3.7-4 cm.
- *Width.*—2.5-3.2 cm.
- *Shape.*—Ovate, with distinct lobes.
- *Base shape.*—Attenuate.
- *Apex shape.*—Acute.
- *Margin.*—5-lobed (palmate), edge shallow dentate.
- *Texture, upper surface.*—Puberulous.
- *Texture, lower surface.*—Pubescent.
- *Color of veins, upper surface.*—RHS 147B.
- *Color of veins, lower surface.*—RHS 147B.
- *Pattern of veining.*—Palmate.
- *Petiole color.*—RHS 147C.
- *Petiole length.*—1.3-1.6 cm.
- *Diameter.*—0.2-0.25 cm.
- *Texture.*—Puberulous.

Stem:
- *Quantity of main branches per plant.*—6 to 8.
- *Color of stem.*—RHS 147B.
- *Length of stem.*—16-18 cm.
- *Diameter.*—0.5 cm.
- *Length of internodes.*—0.5-3 cm.
- *Texture.*—Puberulous.
- *Color of peduncle.*—RHS 147C.
- *Length of peduncle.*—3-4.5 cm.
- *Peduncle diameter.*—0.2 cm.
- *Texture.*—Puberulous.

Inflorescence:
- *Type.*—Compositae, solitary, decorative-type inflorescences borne terminally above foliage, ligulate florets arranged acropetally on a capitulum giving a dubbel daisy flower form.
- *Quantity of short days to flowering (response time).*—Approximately seven weeks.
- *Natural season flowering.*—Mid October.
- *Quantity of inflorescences per plant.*—100-120 (roughly).
- *Lastingness of individual blooms on the plant.*—About five weeks from first color.
- *Fragrance.*—Slightly spicy.

Bud (when showing color):
- *Color.*—Near RHS 5A.
- *Length.*—1.5 cm.
- *Width.*—0.8-1 cm.
- *Shape.*—Prolate.

Immature inflorescence:
- *Diameter.*—3.5-4 cm.
- *Color of ray florets, upper surface.*—RHS 7A.
- *Color of ray florets, lower surface.*—Close to RHS 7C.

Mature inflorescence:
- *Diameter.*—5 cm.
- *Depth.*—2.5 cm.
- *Total diameter of disc.*—No disc present.
- *Receptacle color.*—RHS 137A (deep green).
- *Receptacle height.*—0.4-0.5 cm.
- *Receptacle diameter.*—1.3 cm.

Ray florets:
- *Average quantity of florets.*—Between 100 and 150 in several whorls.
- *Color of florets, upper surface (abaxial).*—RHS 7A.
- *Color inner surface (adaxial).*—RHS 7C.
- *Length.*—2.8 cm.
- *Width/diameter.*—0.5 cm; 0.1 cm for the tube at the base.
- *Shape.*—Spatulate.
- *Apex shape.*—Mostly obtuse.
- *Base shape.*—Tube.
- *Margin.*—Entire, small incisions may occur at the tip.
- *Texture, upper surface.*—Papillate.
- *Lower surface.*—Papillate.

Disc florets: None present.

Phyllaries:
- *Quantity.*—20-25.
- *Color, upper surface.*—RHS 137A.
- *Color, lower surface.*—RHS 137A.
- *Length.*—0.5 cm.
- *Width.*—0.2-0.3 cm.

*Shape*.—Lanceolate.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.3 cm.
*Style color*.—RHS 150B.
*Style length*.—0.2-0.3 cm.
*Stigma color*.—RHS 7A.
*Stigma shape*.—Bi-parted.
*Ovary color*.—RHS 145C.
*Ovary length*.—0.15 cm.
*Ovary width*.—0.1 cm.

Androecium:
*Stamens*.—None, as they are usually present in disc florets only, which are not developed.
*Fertility/seed set*.—Has not been determined to date.
*Disease/pest resistance*.—Has not been determined to date.

What is claimed is:

1. A new and distinct variety of *Chrysanthemum* plant named 'CIFZ00034' substantially as illustrated and described herein.

* * * * *